(12) United States Patent
Wang

(10) Patent No.: US 9,579,475 B2
(45) Date of Patent: *Feb. 28, 2017

(54) TRACHEAL TUBE

(71) Applicant: Benjamin R. Wang, San Jose, CA (US)

(72) Inventor: Benjamin R. Wang, San Jose, CA (US)

(73) Assignee: NEVAP, INC., San Jose, CA (US)

(*) Notice: Subject to any disclaimer, the term of this patent is extended or adjusted under 35 U.S.C. 154(b) by 35 days.

This patent is subject to a terminal disclaimer.

(21) Appl. No.: 14/149,403

(22) Filed: Jan. 7, 2014

(65) Prior Publication Data

US 2015/0101612 A1    Apr. 16, 2015

Related U.S. Application Data

(63) Continuation-in-part of application No. 14/051,443, filed on Oct. 10, 2013, now Pat. No. 9,446,213.

(51) Int. Cl.
A61M 16/04 (2006.01)
A61M 16/08 (2006.01)

(52) U.S. Cl.
CPC .... *A61M 16/0463* (2013.01); *A61M 16/0445* (2014.02); *A61M 16/0459* (2014.02);
(Continued)

(58) Field of Classification Search
CPC .......... A61M 16/0445; A61M 16/0459; A61M 16/0463; A61M 16/0481; A61M 16/0477;
(Continued)

(56) References Cited

U.S. PATENT DOCUMENTS 3,583,404 A    6/1971  McWhorter
3,995,643 A *  12/1976 Merav ................... A61M 16/04
                                              128/207.15

(Continued)

FOREIGN PATENT DOCUMENTS

CN    202699807 U    1/2013
CN    203763615 U    8/2014
(Continued)

OTHER PUBLICATIONS

"International Search Report and Written Opinion of the International Searching Authority", Patent Cooperation Treaty (Jan. 28, 2015), PCT/US2014/059958, 13 pgs.
(Continued)

*Primary Examiner* — Peter S Vasat
(74) *Attorney, Agent, or Firm* — Ascenda Law Group, PC

(57) ABSTRACT

In an embodiment, a tracheal tube system has a first tube, which is flexible. The tube has an opening that is located on the sidewalls. A balloon is attached to the flexible tube. When inflated, the balloon forms a second tube surrounding the first tube with an air space between the first wall of the balloon and the sidewalls of the first tube. The balloon extends covering the opening on the sidewall. Air flowing into the first tube exits, via the third opening into the airspace between the first tube and the balloon, out of the airspace. In another embodiment, the balloon has a tube with multiplicity of holes in the walls is wrapped around the outer wall of the balloon. Negative pressure in the third tube creates suction holding the outer wall of the balloon to walls of the trachea.

10 Claims, 14 Drawing Sheets

(52) U.S. Cl.
CPC ....... *A61M 16/0481* (2014.02); *A61M 16/044* (2013.01); *A61M 16/0816* (2013.01); *A61M 2205/0216* (2013.01); *A61M 2207/00* (2013.01)

(58) Field of Classification Search
CPC .......... A61M 16/0479; A61M 16/0484; A61M 16/0486; A61M 2025/1086; A62B 27/00
See application file for complete search history.

(56) References Cited

U.S. PATENT DOCUMENTS

| | | | |
|---|---|---|---|
| 4,278,081 A * | 7/1981 | Jones | A61M 16/0465 128/207.15 |
| 4,327,721 A | 5/1982 | Goldin et al. | |
| 4,437,856 A | 3/1984 | Valli | |
| 4,693,243 A * | 9/1987 | Buras | A61M 16/04 128/207.15 |
| 4,840,173 A | 6/1989 | Porter, III | |
| 4,973,305 A | 11/1990 | Goltzer | |
| 5,146,916 A | 9/1992 | Catalani | |
| 5,311,864 A | 5/1994 | Huerta | |
| 5,389,074 A | 2/1995 | Parker et al. | |
| 5,513,627 A | 5/1996 | Flam | |
| 5,715,816 A | 2/1998 | Mainiero et al. | |
| 6,048,332 A | 4/2000 | Duffy | |
| 7,669,600 B2 | 3/2010 | Morejon | |
| 8,196,584 B2 | 6/2012 | Maguire | |
| 8,357,118 B2 | 1/2013 | Orr | |
| 8,535,265 B2 | 9/2013 | Burnett et al. | |
| 9,327,091 B2 * | 5/2016 | Wang | A61M 16/0481 |
| 2004/0255951 A1 | 12/2004 | Grey | |
| 2008/0011304 A1 | 1/2008 | Stewart | |
| 2008/0172120 A1 | 7/2008 | Fenn et al. | |
| 2009/0260632 A1 | 10/2009 | Abnousi et al. | |
| 2010/0147309 A1 | 6/2010 | Cuevas et al. | |
| 2011/0023884 A1 | 2/2011 | Cuevas et al. | |
| 2011/0139159 A1 | 6/2011 | Nelson | |
| 2012/0000471 A1 | 1/2012 | Harrington et al. | |
| 2012/0022380 A1 | 1/2012 | Chernomorsky | |
| 2013/0060273 A1 | 3/2013 | Fogarty et al. | |
| 2013/0190706 A1 | 7/2013 | Kleiner | |
| 2014/0033455 A1 | 2/2014 | Vazales et al. | |
| 2015/0101611 A1 * | 4/2015 | Wang | A61M 16/0481 128/207.15 |
| 2015/0101612 A1 | 4/2015 | Wang | |

FOREIGN PATENT DOCUMENTS

| | | |
|---|---|---|
| CN | 203763616 U | 8/2014 |
| DE | 202009016034 U1 | 3/2010 |
| WO | 9321816 A1 | 11/1993 |
| WO | 9640339 A1 | 12/1996 |
| WO | 2007130579 A2 | 11/2007 |
| WO | 2012/087837 A1 | 6/2012 |

OTHER PUBLICATIONS

Teleflex, Inc, Teleflex ISIS HVT, the First Convertible Endotracheal Tube, Date Retrieved Oct. 29, 2014, 2 pages.
Smiths Medical, SACETT Suction Above Cuff ET Tube, Date Retrieved Oct. 29, 2014, 9 pages.
Kimberly-Clark Worldwide, Inc, KIMVENT Closed Suction Systems, Date Retrieved Oct. 29, 2014, 4 pages.
Covidien, TaperGuard Endotracheal and Specialty Tubes, 2014,Date Retrieved Oct. 29, 2 pages.

* cited by examiner

TRACHEAL TUBE

PRIORITY CLAIM

This application is a continuation-in-part of U.S. patent application Ser. No. 14/051,443, entitled "TRACHEAL TUBE," filed Oct. 10, 2013, and the above listed application is incorporated herein by reference, in its entirety

FIELD

This specification generally relates to the field of tracheal tubes.

BACKGROUND

The subject matter discussed in the background section should not be assumed to be prior art merely as a result of its mention in the background section. Similarly, a problem and the understanding of the causes of a problem mentioned in the background section or associated with the subject matter of the background section should not be assumed to have been previously recognized in the prior art. The subject matter in the background section may merely represents different approaches, which in and of themselves may also be inventions.

Tracheal tubes with inflatable balloon with suction means are broadly known in the prior art. However, the suctioning means of such prior arts are inefficient with suctioning secretions above and around the balloon, therefore allowing secretions and/or pathogens to travel through the balloon and tracheal walls and into the airflow of the tracheal tube. In certain situations, the secretions/pathogens get aerosolized by the high velocity of the ventilated air traveling through the tracheal tube and into the patient's lungs. Aerosolized pathogens traveling at high velocity may send the pathogens deep into the lungs which may cause Ventilator Associated Pneumonia (VAP).

BRIEF DESCRIPTION OF THE FIGURES

In the following drawings like reference numbers are used to refer to like elements. Although the following figures depict various examples of the invention, the invention is not limited to the examples depicted in the figures.

DETAILED DESCRIPTION

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

In general, at the beginning of the discussion of each of FIGS. 1-5 is a brief description of each element, which may have no more than the name of each of the elements in the one of FIGS. 1-5 that is being discussed. After the brief description of each element, each element is further discussed in numerical order. In general, each of FIGS. 1-5 is discussed in numerical order and the elements within FIGS. 1-5 are also usually discussed in numerical order to facilitate easily locating the discussion of a particular element. Nonetheless, there is no one location where all of the information of any element of FIGS. 1-5 is necessarily located. Unique information about any particular element or any other aspect of any of FIGS. 1-5 may be found in, or implied by, any part of the specification.

Figure 1:
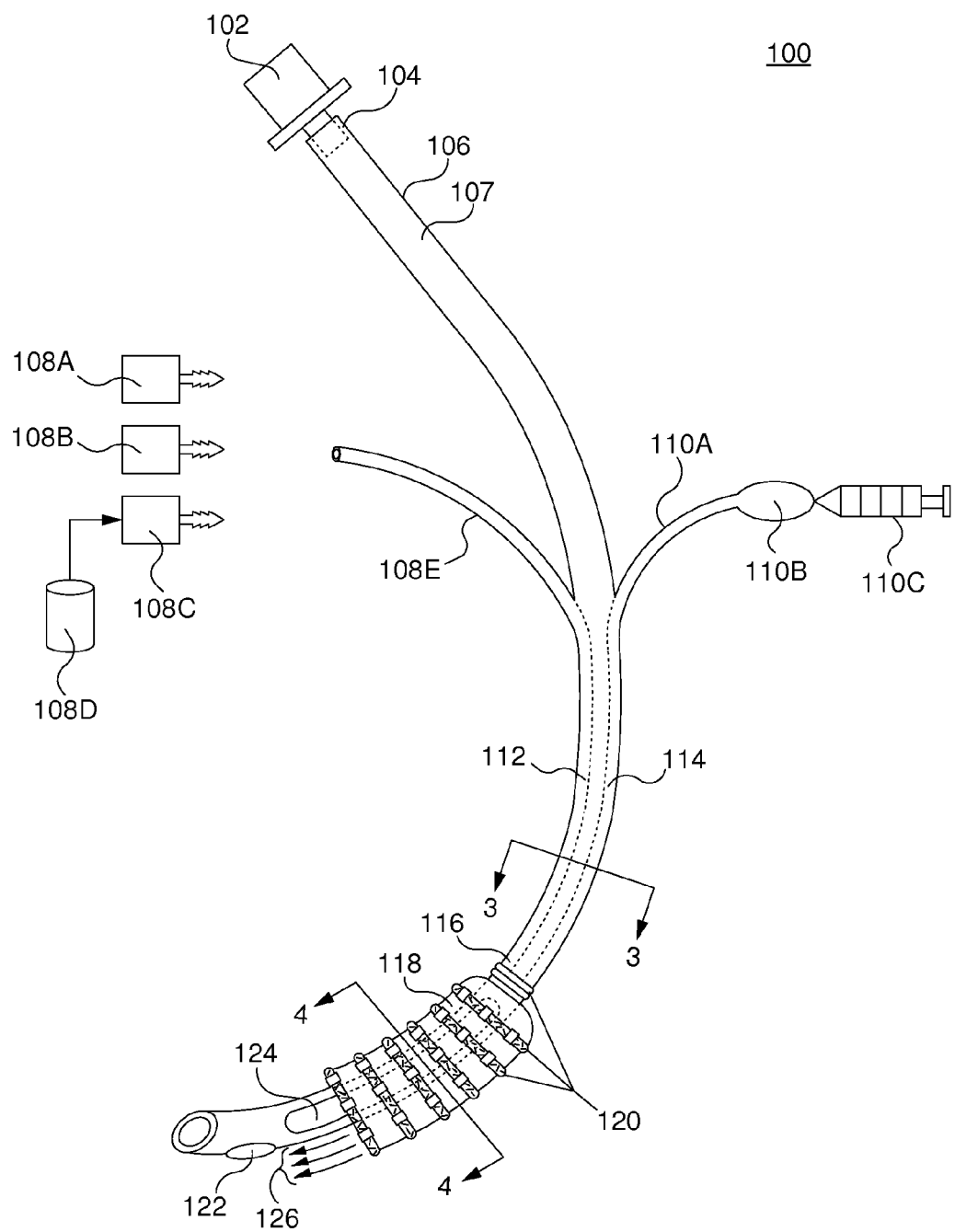
FIG. 1 shows a diagram of an embodiment of a tracheal tube.

FIG. 1 shows a diagram of an embodiment of a tracheal tube system 100. The tracheal tube system 100 may include at least one connector 102, a catheter 106 having opposed open proximal end 104 and open distal end 122, a suction device 108a, an air dispensor device 108b, a fluid dispensor device 108c, a fluid reservoir 108d, at least one suction tube 108e, at least one inflation tube 110a, a pilot balloon 110b, inflation fluid supplying device 110c, at least one suction tube lumen 112, at least one inflation tube lumen 114, at least one suction line exit 116, at least one balloon 118, at least one suction line 120, at least one enlarged opening 124, and at least one enlarged air passage way 126. In other embodiments the tracheal tube system 100 may not have all of the elements or features listed and/or may have other elements or features instead of or in addition to those listed.

The tracheal tube system 100 is a tracheal tube with a 360 degree suction line and an enlarged airflow passage. In an embodiment, suctioning is set at 15 mm Hg negative pressure. The tracheal tube system 100 may be adapted to be used for various tubes such as endotracheal, endobronchial, and tracheostomy tubes. The endotracheal tube 100 is a catheter that is inserted into the trachea through the mouth or nose in order to maintain an open air passage or to deliver oxygen, medications, or to permit the suctioning of mucus or to prevent aspiration of oral secretions. Endotracheal tube 100 may be a flexible, hollow cylindrical tube that is open at both ends to allow air to pass through.

The connector 102 is a connection adapted to connect to a mechanical ventilator. The connector 102 attaches the tracheal tube system 100 to a mechanical ventilator. In an embodiment, the connector 102 may have a length of 4 cm, a proximal Outer Diameter (OD) of 1.5 cm, a proximal Inner Diameter (ID) of 1.3 cm, and a proximal length of 1.5 cm. The cross-sectional area of the safety (which is the collar) is 1.5 cm×2.5 cm. In an embodiment, the length of the safety is 0.5 cm. In an embodiment, the distal opening OD of connector 102 is 0.8 cm. In an embodiment, the distal length of connector 102 is 2 cm. In an embodiment the tolerance for all of the listed dimensions in this specification is +/−10% of the value of the dimension in question. In another embodiment the tolerances in this specification is +/−5% of the dimension in question. In an embodiment, the connector 102 is made from hard polypropylene. In other embodiments, the mechanical ventilator may be replaced with an air bag if a mechanical ventilator is not available.

The proximal end 104 is the end of the tracheal tube system that is not intubated inside the patient. In this specification, to intubate a patient refers to placing a tube in the patient. For example, intubulating a patient may refer to the inserting a breathing tube into the trachea for mechanical ventilation. The proximal end 104 is open and connected to the end of the connector 102 opposite the mechanical ventilator. In an embodiment, the proximal end 104 has a length of 31 cm. In an embodiment, the proximal end 104 is made from flexible polyvinylchloride.

The catheter 106 is a tube that is inserted into the body in order to aid delivery of medications. The catheter 106 may be inserted into the trachea to deliver oxygen. The catheter 106 may be made from a tube. The catheter 106 may be made out of plastic (e.g., polyvinyl chloride, PVC). The plastic materials may be visually clear or opaque. Since plastic is not radio opaque, the catheter 106 may have a line of radio opaque material that makes the tube more visible on a chest X-ray. In other embodiments, the catheter 106 may be made out of wire-reinforced silicone rubbers. Yet in other embodiments, the catheter 106 may be made out of silicone rubber, latex rubber, or stainless steel. The different materials used to make a tracheal tube usually depends on the application of the tube that is required. For example, a wire-reinforced silicone rubber catheter is quite flexible yet difficult to compress or kink, making the wired-reinforced silicone rubber catheter useful for situations in which the trachea is anticipated to remain intubated for a prolonged duration, or if the neck needs to remain flexible during surgery.

The catheter 106 have an inner diameter and an outer diameter. The "size" of a tracheal tube refers to the inner diameter of the catheter. For example, if someone asks for a "size 6" tracheal tube, they are asking for a tracheal tube with an inner diameter of 6 mm. Furthermore, the inner diameter may be labeled on the catheter 106 as "ID 6.0." Narrower tubes increase the resistance to gas flow. For example, a size 4 mm tube has sixteen times more resistance to gas flow than a size 8 mm tube. The additional resistance can be especially relevant in the spontaneously breathing patient who will have to work harder to overcome the increased resistance. Therefore, when choosing the appropriate "size", the largest size that is suitable for a given patient is typically recommended. For human beings, the size of the catheter 106 may range from 2.0 mm for neonates to 10.5 mm for adult males. The catheter 106 may have an OD of 0.7 cm to 0.9 cm (depending on the size of the patient).

The catheter 106 may have varying lengths depending on who or what is using the catheter 106. The length of the catheter 106 is measured from the end that goes into the trachea. The length of the catheter may vary if the catheter 106 is inserted orally or through the tracheostomy stoma. For human beings with an oral insertion, the length of the catheter 106 may range from 7.5 cm for neonates to 23 cm for adult males. In an embodiment, the catheter 106 may be inserted orally or nasally as an endotracheal tube.

In another embodiment, the catheter 106 may be inserted into a tracheostomy stoma and used in a tracheostomy. A tracheostomy is an opening through the neck into the trachea through which a tube may be inserted to maintain an effective airway and help a patient breathe. A tracheostomy stoma is the actual opening. When the catheter is used in a tracheostomy, the length of the catheter 106 may be shorter.

The primary channel 107 is the main passageway of the catheter 106 for delivering gases containing oxygen to a patient or for extracting carbon dioxide ($CO_2$) from a patient. The OD of primary channel 107 is variable from 0.6 cm to 0.8 cm. In an embodiment, the diameter of the primary channel 107 is the same as the inner diameter of catheter 106.

The suction device 108a is a machine that can be used to remove mucous and other unwanted fluids from a patient. The suction device 108a creates a negative pressure in order to extract mucous and other unwanted fluids from a patient. The suction device 108a may have a varying power of suction. The suction device 108a may run continuously at a low power of suction setting to provide a constant suction. The suction device 108a may run on an as needed basis, depending on the situation of application.

The air dispensor device 108b is a machine that can be used to pump air. The air dispensor device 108b may be an electronically powered air dispensor or a manual air pump such as a syringe filled with air.

The fluid dispensor device 108c is a machine that is used to pump fluid. The fluid dispensor device 108c may be an electronically powered fluid dispensor with varying or fixed power of dispensing. The fluid dispensor device 108c may also be a manually operated device such as a syringe filled with a fluid.

The fluid reservoir 108d is a reservoir for storing rinsing fluid to dispense into a patient to help loosen mucous build up to allow for an easier extraction. The fluid reservoir may be water to be used as a cleaning agent and/or may include another cleaning agent, or may be saline or an antibiotic rinse. The fluid reservoir 108d may be the fluid source for the fluid dispenser device 108c. In some embodiments, fluid dispenser device 108c may not need to draw from the fluid reservoir of 108d.

The suction tube 108e is a tube adapted to suction secretion collected inside the border of the cuff and trachea region around the tracheal tube. The border of the cuff and trachea region is the part of the cavity of the larynx below the true vocal chords. The suction tube 108e may be adapted to connect to a suction device to suction the secretion. In some embodiments, the suction tube 108e may be attached to the catheter 106 proximal to the open proximal end 104. In other embodiments, the suction tube 108e may extend into the inner walls of the catheter 106. The suction tube 108e length is 24 cm. The suction tube 108e may be made from flexible polyvinylchloride.

In another embodiment, the suction tube 108e may be adapted to connect to an air dispensing device 108b to dispense air into the suction tube 108e to clear out the suction tube.

In yet other embodiments, the suction tube 108e may be adapted to connect to a fluid dispensor device 108c to provide a rinsing fluid. The fluid dispensor device may draw the rinsing fluid from the fluid dispensing reservoir 108d. The purpose of the rinsing fluid may be to loosen up the secretion and mucous surrounding the border of the cuff and trachea region around the trachea to loosen mucous which may collect around the tracheal tube. Once the rinsing fluid has been introduced, suction may be restored to the suction tube 108e and the liquid and any secretions that may have been loosened or dissolved may be removed. The introduction of a rinsing fluid procedure may be repeated as deemed necessary and it is performed at the discretion of the caregiver or user in order to clean secretions and other liquids that may collect and potentially clog the suction. The rinsing fluid may comprise water, saline, as well as other biocompatible liquids or mucolytic agents. A mucolytic agent is an agent which dissolves thick mucus and is usually used to help relieve respiratory difficulties. It does so by dissolving various chemical bonds within secretions, which in turn can lower the viscosity by altering the mucin-containing components.

The inflation tube 110a is a tube used to supply an inflation fluid. In an embodiment, the inflation tube 110a length is 24 cm. In an embodiment, the inflation tube is made from flexible polyvinylchloride.

The pilot balloon 110b is a balloon that provides an indication of the air pressure that exists in another balloon that it is connected to. Furthermore, the pilot balloon 110b has a one way valve that prevents air inflated into the pilot balloon 110b from deflating because of the one way valve design. The pilot balloon 110b may serve as a balloon deflator when the pilot balloon 110b is pressed, thus turning the one way valve into a two way valve.

The inflation fluid supplying device 110c is a device that delivers an inflation fluid. The inflation tube 110a may be connected to the inflation fluid supply device 110c by way of pilot balloon 110b. The fluid supplying device 110c may be a syringe or a pump. The inflation fluid may be a gas or a liquid, depending on the desired functionalities of the inflation fluid. The inflation fluid may be air. The inflation fluid may also be a methylene blue coloured saline. For example, some airway surgery involves the use of laser beams to burn away tissue. These beams can ignite ordinary endotracheal tubes and in the presence of Oxygen may cause major airway fires. If the laser manages to damage the balloon, the coloring will help identify rupture and the saline will help prevent an airway faire.

The suction tube lumen 112 is an extension of the suction tube 108e that extends along the length of the catheter 106. The suction tube lumen 112 further provides suction to the tracheal tube from the suction tube 108e. The suction tube lumen 112 may be connected to the suction tube 108e or it may be an extension of suction tube 108e that is connected to the catheter 106. The suction tube lumen 112 may also extend along the length and inside the walls of catheter 106. In another embodiment, the suction tube lumen 112 may attach to the exterior surface of the catheter 106 and extend along the length of the catheter 106. In other embodiments, the suction tube lumen 112 may provide rinsing fluids from the suction tube 108e.

The inflation tube lumen 114 is an extension of the inflation tube 110 that extends along the length of the catheter 106. The inflation tube lumen 114 may be connected to the inflation tube 110. The inflation tube lumen 114 may also be an extension of the inflation tube 110 that extends along the length and inside the wall of the catheter 106. In another embodiment, the inflation tube lumen 114 may attach to the exterior surface of the catheter 106 and extend along the length of the catheter 106.

The suction lumen exit point 116 is the point where the suction lumen 114 emerges from the catheter 106. The suction lumen exit point 116 is strategically located along the length of the catheter 106 so that it is proximal to the location where secretion accumulates in the region bordering the cuff and trachea above the balloon.

The balloon 118 is an inflatable resilient cuff. The balloon 118 serves as a seal between the tracheal tube and the patient's trachea wall to allow for positive pressure ventilation. Positive pressure ventilation is a mechanical ventilation in which air is delivered into the airways and lungs under positive pressure, usually via an endotracheal tube, producing positive airway pressure during inspiration. The balloon 118 may be made from various compositions of rubber or elastic polymer polyurethane. The thickness and elasticity of the rubber material may vary, depending on the intended use of the balloon 118. In an embodiment, the balloon 118 is 5 cm long and 3 cm in diameter. Excluding rare errors in calcium metabolism, most human male and female trachea diameters fall between 25-29 mm and 23-27 mm, respectively. In an embodiment, the seal between each chamber is not complete so as to allow air to flow from one balloon to the next (the opening between chambers may be the width of the balloon and between 0.1-0.5 cm high). In some embodiments, the balloon 118 may be a high pressure, low volume balloon. In other embodiments, the balloon 118 may be a low pressure, high volume balloon. Depending on the intended purpose and use of the balloon, the appropriate material is used. When introduced into the patient, the balloon 118 is initially deflated. Once the tracheal tube system 100 is placed inside the patient's trachea, the inflation tube 110 may be adapted to a fluid supplying device to inflate the balloon 118. The balloon 118 is connected to the inflation lumen 114. Once the balloon 118 is inflated, the shape and expanded size of the balloon 118 creates a seal against the tracheal wall, thereby preventing gases being pumped into the lungs via the catheter 106 from backing up around the tube and escaping through the tracheal tube, thereby providing a positive pressure ventilation. The inflation of the balloon 118 creates a seal to provide a positive pressure necessary to artificially ventilate the lungs.

The balloon 118 is attached to the catheter 106 between the suction lumen exit 116 and the distal end 122. The balloon 118 is completely sealed to the catheter 106 at the end of the balloon distal to the suction lumen exit 116. However, the opposite end of the balloon 118 is not sealed to the catheter 106. Instead, the balloon 118 proximal to the open distal end 122 is cylindrical shaped. The balloon, when not attached to a tracheal tube resembles the shape of a bottle without the bottom portion of the bottle. The shape of the balloon is created by the balloons circular chambers and the size of chambers can vary, the largest balloon is first and the size of the balloons decreases along the direction going towards the lungs. For example, in an embodiment, the balloon 118 diameters of the chambers, in order from proximal to distal, are 3 cm, 1 cm, 0.6 cm, 0.4 cm, 0.2 cm, and 0.1 cm, respectively.

In another embodiment, the balloon 118 may extend from the open distal end 122 along the length of catheter 106 and ending proximal to the connector 102.

Tracheal tubes with balloon 118 may present a problem in that secretions produced above the balloon 118 may be prevented from flowing along the channel of the esophagus or trachea and thereby collect above the balloon 118, providing a site for the possible accumulation of pathogens. Occasionally, these pathogens may find their way through the cuff created by balloon 118 and end up below the cuff near the open distal end 122. Once the pathogens make it through the balloon 118, the pathogens may find their way into the patient's lungs and create harmful infection. The accumulation of secretion above the balloon 118 may present other problems as well.

The suction line 120 is a tube with many small holes distributed all around the tube and all along the tube length. In an embodiment, the suction line 120 is 20 cm in length. The small holes allow the suction and removal of secretion fluid that comes in contact with the suction line 120. The suction line 120 may be an extension of the suction tube 108e and the suction tube lumen 112. The suction line 120 emerges from within the catheter 106 walls at the suction lumen exit point 116. The connection point between the balloon 118 and the catheter 106 proximal to the suction line 120 may be 0.5 cm-1.5 cm above the balloon 118 to ensure a secure seal of the balloon 118 to the catheter 106. The suction line 120 is wrapped around the catheter 106 and above the balloon 118. The suction line 120 wrap provides a 360 degree suction of secretion fluids that collect in the space above the balloon 118 and within the patient's trachea (area bordered by the cuff and trachea) without negatively impacting ventilation of the patient at the level of the cuff suction line attached to balloon.

The suction line 120 may also wrap around the balloon 118. The suction line 120 may wrap around the balloon 118 multiple times before terminating at a distal point of the exterior surface of balloon 118. The suction line 120 provides suction of secretions that collect in the spaces between the balloon 118 and the patient's trachea. The suction line 120 may also provide additional sealing properties between the balloon and the tracheal wall within the patient when there is negative pressure within the suction line 120.

The suction line 120 may also coil around the balloon 118 within predefined sleeves on the balloon 118 outer surface. The sleeves will be further discussed in FIG. 5.

In other embodiments, the suction line 120 may also distribute a rinsing fluid when the suction tube 108e is adapted to connect to a fluid dispensing device to dispense a rinsing fluid. The rinsing fluid flows through the small holes scattered and is dispersed along the suction line 120.

The open distal end 122 is the opening at the end of the tracheal tube system 100. In most embodiments, the open distal end 122 is the end that resides inside the patient's tracheal area and the open distal end 122 is where the mechanical ventilator's air, traveling through the primary channel 107 may enter the patient's lungs. When the tracheal tube system 100 is intubated inside a patient, the open distal end 122 of the catheter 106 is situated within the upper respiratory system of the patient. In current use, the open distal end 122 serves as the primary air passage way for mechanically ventilating a patient, with an opening in the sidewall of catheter 106 as the secondary source of air passage in the event the open distal end 122 is blocked. In the current embodiment, the open distal end 122 will still serve as an air passage way.

The enlarged opening 124 provides an alternative air flow source to the patient's lungs in the event the open distal end 122 is blocked or obstructed. The enlarged opening 124 serves as the primary source of air flow into the patient's lungs since the enlarged opening 124 has an opening considerably larger than the open distal end 122. The airflow from enlarged opening 124 comes into contact with the interior layer of the balloon 118. The inflated balloon 118 creates a cuff along the tracheal wall to prevent the escape of air pressure between the patient's lung and the tracheal tube system 100. The airflow that comes out of the enlarged opening 124 may flow around the inner layer of the balloon 118 and get redirected towards the patient's lung. The enlarged opening 124 may have a length that is slightly longer along the length of the catheter 106 than the balloon 118 such that the opening 124 may start from a point proximate to the 360 degree seal of the balloon 118 with the catheter 106 proximal to the suction lumen exit 116 and extend beyond the point where the balloon 118 ends proximal to the distal end 122. The width of the enlarged Opening 124 may be adjusted to create a larger cross sectional area of air flow to travel between the patient's lungs and the catheter 106.

In another embodiment, where the length of the balloon 118 may extend from proximal to the the open distal end 122 along the length of catheter 106 and terminate proximal to proximal open end 104, the length of the enlarged opening 124 may extend along the length of the entire catheter 106 to provide a larger amount of area for airflow to travel between the primary channel 107 and the patient's lungs.

The enlarged air passage way 126 is a passage way through which fluids pass between the patient's trachea and the tracheal tube system 100. The enlarged air passage way 126 may be determined by taking the cross-sectional area measured by the inner diameter of the inflated balloon 118 and subtracting the cross-sectional area of the catheter 106. The enlarged air passage way 126 allows the same amount of air volume to move into the patient's lungs but at a slower velocity as compared to prior devices.

The velocity at which a volume of air flows through a pipe may be increased or decreased based on the diameter of the pipe. Decreasing the input velocity increases particle size, decreases the aerosolization, and decreases microspeciation. The diameter of the pipe defines the cross-sectional area available for the volume of air to flow through. The velocity of a volume of air flows through a passage way may be reduced if the diameter of the passage way is increased. Likewise, when the diameter of the passage way is reduced, to move the same fixed volume of air through the reduced diameter passage way, the velocity at which the volume of air flows must be increased to move the same fixed volume of air through the reduced diameter passage way. The increased diameter of the passage way will increase the cross-sectional area for air to travel through. With a larger cross-sectional area for air to travel through the tracheal tube system 100 based on the enlarged air passage way 126 created by the shape of the balloon 118 proximal to the open distal end 122, the same volume of air that needs to flow into the lung(s) at the enlarged air passageway 126 may be delivered to the lung(s) at a reduced velocity. The volume of air that flows through from the enlarged opening 124 located within the balloon 118 is delivered to the lungs through the enlarged air passageway 126. The reduction in velocity of airflow at the enlarged air passage way 126 helps to address a common cause of issues with tracheal procedures, such as Ventilator Associated Pneumonia (VAP). VAP can be minimized by eliminating the "aerolization" of foreign bodies that shoot into the lower area of the lungs from the high speed of the ventilator. Currently, the "aerolization" of foreign body traveling at high velocity into the lungs is due to the small cross sectional area of the traditional tracheal tube. The smaller the cross sectional area of the tube, the higher the velocity is required to move the same volume of air. The enlarged air passage way 126 may allow the appropriate amount of air to travel into the patient's lungs at a reduced velocity of airflow that in turn may help to reduce VAP. In an embodiment, the length of the air passage way 126 is 4.5 cm, whereas in contrast a standard Murhpy's Eye is 1.0 to 1.5 cm.

Figure 2A:
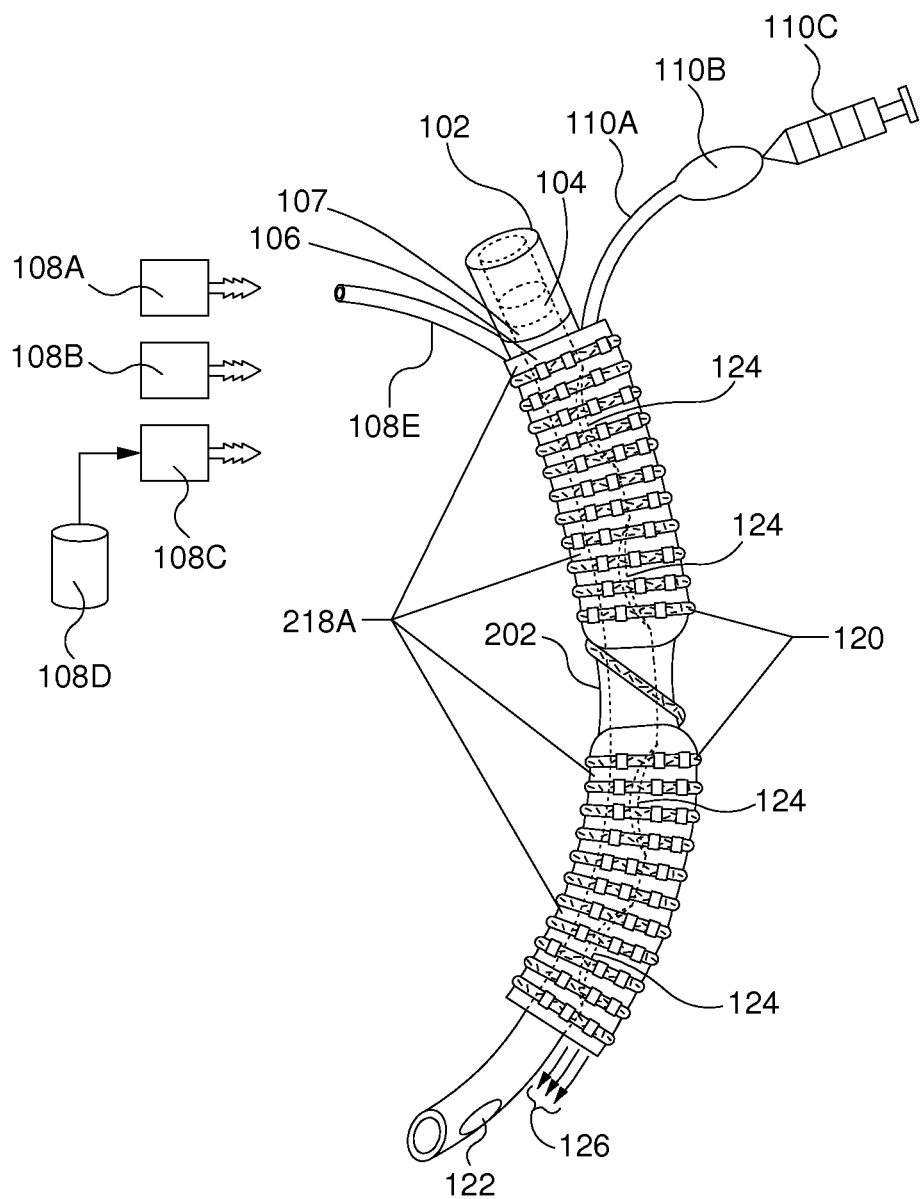
FIG. 2A shows a diagram similar to that of FIG. 1 but illustrating another embodiment of a tracheal tube.
Figure 2B:
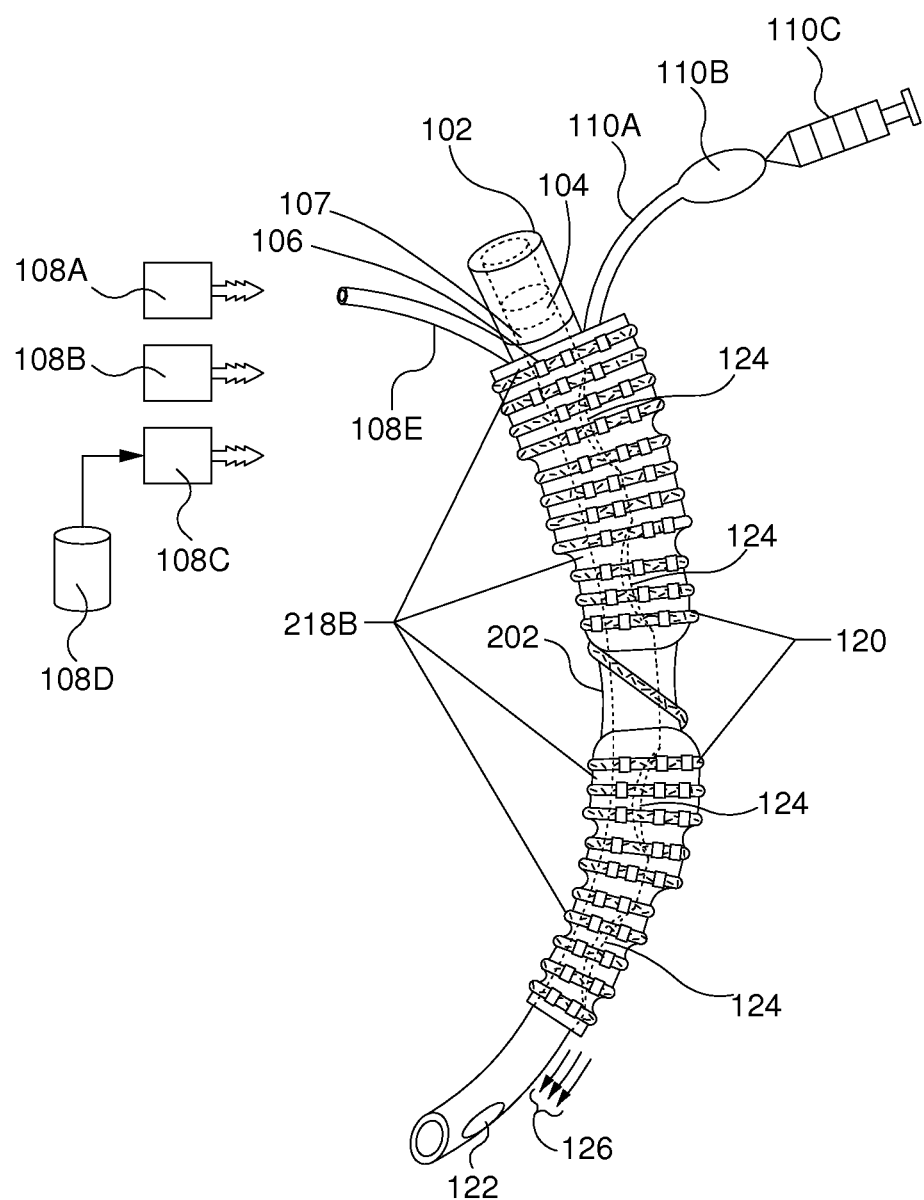
FIG. 2B shows a diagram yet another embodiment of a tracheal tube.

FIGS. 2A and 2B show a diagram similar to that of FIG. 1 but illustrating other embodiments of a tracheal tube. The tracheal tube system 200a and 200b may include the following elements, as explained in FIG. 1, at least one connector 102, a catheter 106 having opposed open proximal end 104 and open distal end 122, a suction device 108a, an air dispensor device 108b, a fluid dispensor device 108c, a fluid reservoir 108d, at least one suction tube 108e, at least one inflation tube 110a, a pilot balloon 110b, an inflation fluid supplying device 110c, at least one suction line 120, a plurality of enlarged opening 124, at least one enlarged air passage way 126, and at least one balloon 218a (FIG. 2A) or 218b (FIG. 2B). In other embodiments the tracheal tube system 200 may not have all of the elements or features listed and/or may have other elements or features instead of or in addition to those listed.

Furthermore, the tracheal tube system 200a and 200b may also include a vocal chord crease 202. The vocal chord crease 202 is a portion of the balloon 118 that is narrow and extends for an amount necessary to clear the vocal chord of the patient. The purpose of the vocal chord crease 202 is to minimize contact between the tracheal tube system 200 and the patient's vocal chord. The balloon 218a or 218b in the current embodiment extends along approximately the entire length of the catheter 106. Other than the length of the balloon 218a or 218b and the crease in the balloon 218a or 218b at the vocal chord crease 202, the balloon 218a or 218b is essentially the same as the embodiment described in FIG. 1. No balloons are located in the crease to avoid direct pressure on the vocal chords. The crease is suspended off the vocal cords by balloons on either end of the crease, and in an embodiment, the crease is color coded so that medical personnel can see where to position the crease.

The plurality of the enlarged openings 124 is the primary air flow channel for the ventilation of the patient. The plurality of the enlarged openings 124 allows the velocity of the airflow between the patient's lungs and the tracheal tube system 200 to be comparable to the velocity of the airflow the patient would experience without an artificial ventilation system.

In an embodiment, balloon 218a or 218b forms a tube surrounding and attached to catheter 106, which is open at both ends, so that air may enter one end of the the tube formed by balloon 118 and exit the other end of the tube formed by balloon 218a or 218b. When one end of endotracheal tube system 200a or 200b is placed within a patient, air may enter the patient via both the tube formed by balloon 218a or 218b, respectively, and catheter 106, so that air may enter and travel into the patient through a larger cross sectional area than were balloon 218a or 218b not present or crossed.

Endotracheal tube systems 200a and 200b differ from one another in that the sections of balloon 218a all have the same diameter, whereas the sections of balloon 218b have decreasing diameters. In an embodiment, the largest segment of balloon 218b has an outer diameter 5 cm, the narrowest segment has an outer diameter of 1.5 cm, and the segments in between monotonically decrease in diameter from 5 cm to 1.5 cm going form the end of the endotracheal tube 200b that is furthest from the lungs toward the end that is closest to the lungs.

Figure 3:
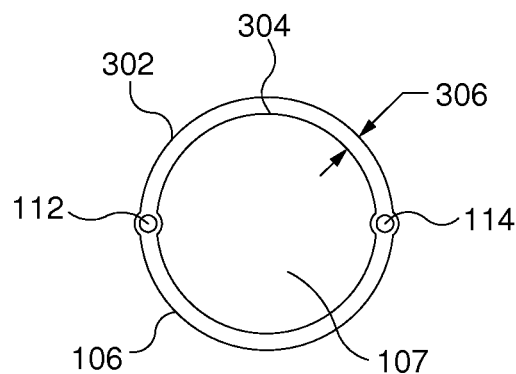
FIG. 3 shows a cross-sectional view of an embodiment of the catheter of FIG. 1 taken longitudinally through the catheter along the 3-3 cut line of FIG. 1.

FIG. 3 shows a cross-sectional view 300 of an embodiment of the catheter of FIG. 1 taken longitudinally through the catheter at 3-3. The cross-sectional view 300 may include an exterior surface 302, an interior surface 304, a wall thickness 306, a catheter 106, suction lumen 112, inflation lumen 114, and primary channel 107.

The catheter 106, suction lumen 112, inflation lumen 114, and primary channel 107 were discussed in FIG. 1. The exterior surface 302 is the exterior surface of catheter 106. The interior surface 304 is the interior surface of the catheter 106. The wall 306 is the tube thickness determined by the exterior surface 302 and the inner surface 304. The thickness of the wall 306 may vary based on the different uses and application of the tracheal tube system 100.

The suction lumen 112 may be an extension of the suction tube 108e (from FIG. 1) wherein the suction lumen 112 is configured to run along the inside of the wall 306. In another embodiment, the suction lumen 306 may be attached to run along the exterior surface 302 of the catheter 106.

The inflation lumen 114 may be an extension of the inflation tube 110a (from FIG. 1) wherein the inflation lumen 114 is configured to run along the inside of the wall 306. The inflation lumen 114 may be situated opposite the suction lumen 112. In another embodiment, the inflation lumen 114 may be configured to run along the exterior surface 302 of the catheter 106.

Figure 4:
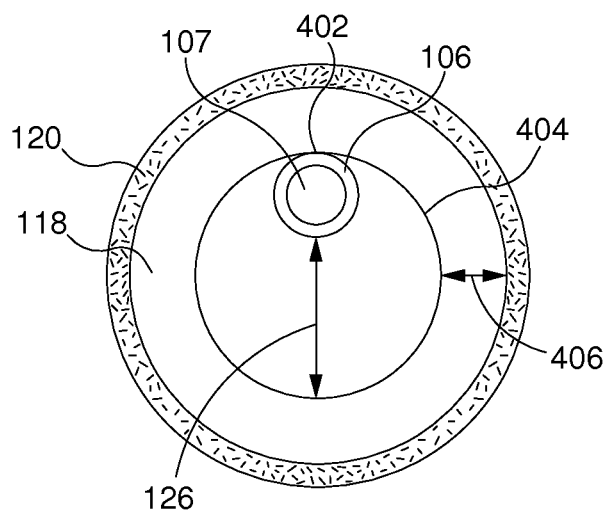
FIG. 4 shows a cross-sectional view of an embodiment of a catheter and a balloon of FIG. 1 taken longitudinally through the catheter and the balloon along the 4-4 cut line of FIG. 1.

FIG. 4 shows a cross-sectional view 400 of an embodiment of a catheter 106 and a balloon 118 of FIG. 1 taken longitudinally through the catheter 106 and the balloon 118 at 4-4. The cross-sectional view 400 may include a spinal sealant 402, a balloon inner layer 404, a balloon thickness 406, and a catheter 106. Furthermore, cross-sectional view 400 may also include a primary channel 107, a balloon 118, a suction line 120, and an enlarged airway passage 126; all of which are further defined in FIG. 1.

The spinal sealant 402 is the contact point along the outer surface of the catheter 106 and the inner surface of balloon 118. The balloon inner layer 404 is the inner layer of the balloon 118. The balloon thickness 406 is the thickness of the balloon 118 when fully inflated. The balloon thickness 406 may be a variable in the enlarged airway passage 126. The thicker the balloon, the smaller the enlarged airway passage. Likewise, the thinner the balloon thickness 406, the larger the enlarged airway passage 126. The balloon thickness 406 may vary to provide the appropriate amount of enlarged airway passage 126. The spinal sealant 402 is designed to not have any contact with the enlarged opening 124.

The spinal sealant 402 connection point may extend the length of the catheter 106 (which is situated inside the balloon 118) to create a secure attachment between the balloon 118 and the catheter 106. In an embodiment, the spinal sealant 402 may be located opposite the enlarged opening 124 located on the catheter 106, so that the enlarged opening 124 is not in contact with the inner wall of the balloon 118. The spinal sealant 402 may be glued to the inner walls of balloon 118. In another embodiment, the spinal sealant 402 may be heat infused by melting the inner wall of the balloon 118 along the spinal sealant 402 together. The airflow that comes out of the enlarged Murhpy's Eye will travel through the catheter 106 by way of the primary channel 107 and exit the catheter 106 in one of two locations: 1) at the open distal end 122 or 2) at the enlarged opening 124. The air exiting the enlarged opening 124 eventually flows through the enlarged air passage way 126.

Figure 5:
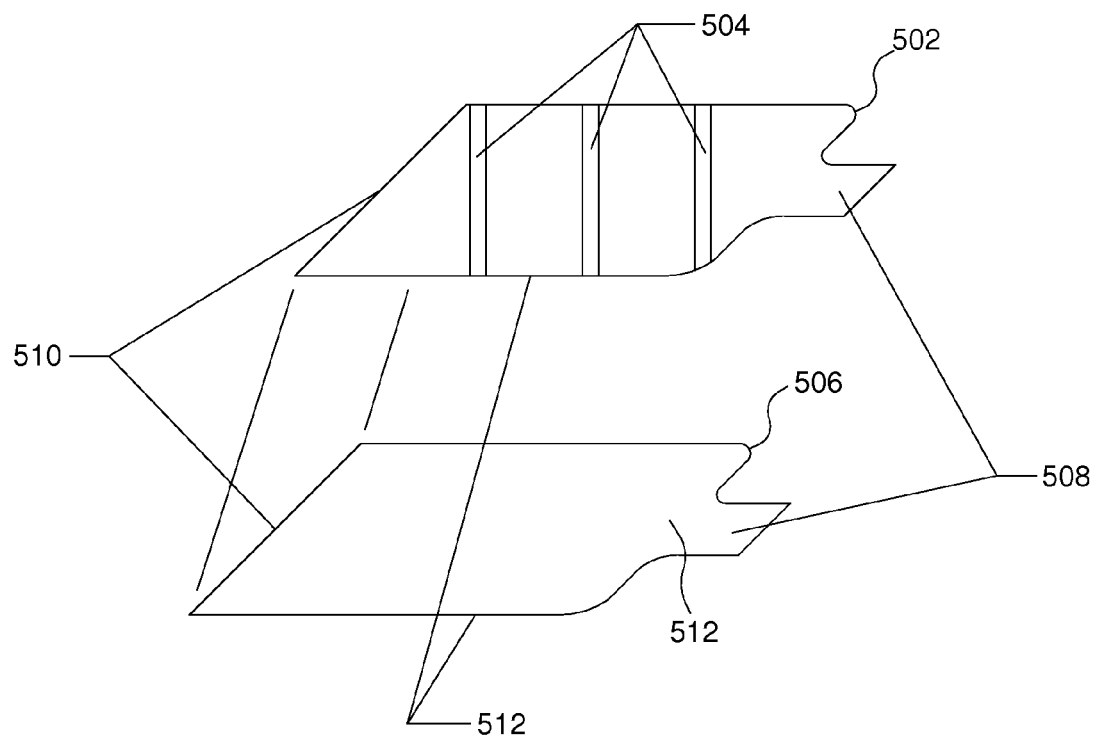
FIG. 5 shows a drawing of an embodiment of an assembly of a balloon.

FIG. 5 shows an embodiment of the balloon assembly 500. The balloon assembly 500 may include an outer balloon sheet 502, a plurality of sleeves 504, an inner balloon sheet 506, a tube connection point 508, a distal edge 510, and an inflation connection point 512.

The outer balloon sheet 502 is the exterior layer of the balloon 118 that comes into contact with the patient's tracheal walls. The outer balloon sheet 502 is generally a rubber material with various thickness and elasticity, depending on the application of the balloon. For example, the balloon 118 may be adapted to be used in as a low volume, high pressure cuff or a high volume, low pressure cuff. In a low volume, high pressure application, the material of the balloon may be slightly thicker and less elastic whereas in a high volume, low pressure application, the material may be thinner and more elastic.

The plurality of sleeves 504 are like channels arranged parallel to one another in a diagonal configuration with respect to the outer balloon sheet 502. The sleeves 504 are aligned diagonally in such a way that when the outer balloon sheet 502 is curled into a cylindrical shape, the sleeves 504 line up at the connection point to create a a single helical groove around the cylindrical shape of the outer balloon sheet. Once the sleeves 504 are aligned, the sleeves may allow the suction line 120 to wrap around the balloon 118 in an organized and predictable form because the suction line 120 fits neatly into the sleeves. Once the suction line wrap 120 is wrapped around the balloon 118 within the sleeves 504, the suction line wrap 120 may provide a slight protrusion over the balloon surface. The protrusion provides a more secure and stable seal between the balloon 118 and the patient's tracheal wall because the suction effect created by the suction line wrap 120 around the balloon 118 helps to securely seal the balloon with the tracheal walls.

The inner balloon sheet 506 is the inner layer of the balloon 118. The inner balloon sheet 506 when attached to the outer balloon sheet 502 allows the balloon 118 to take form. The tube connection point 508 is the portion of the balloon 118 that attaches the balloon 118 to the tracheal tube. The tube connection point 508 is the only portion of the balloon 118 that attaches to the tracheal tube. The attachment is a 360 degree tight seal around the tube. When the outer balloon sheet 502 and inner balloon sheet 506 are attached, the tube connection point 508 is sealed tight to not allow any air to travel in between the two sheet because the purpose of the connection point 508 is attach the balloon 118 to the tracheal tube.

The distal edge 510 is the edge of the outer balloon sheet 502 and inner balloon sheet 506 that is opposite the tube connection point 508. The distal edge 510 is the section of the outer and inner balloon sheets that is sealed together to create a balloon shape.

The longitudinal edge 512 is the edge that runs along the balloon longitudinally. One end of the edge is the distal edge 510 and the other end of the edge is the connection point 508. The longitudinal edge 512 of the inner balloon sheet 506 will be the edge that seals to the opposing longitudinal edge 512 of the inner balloon sheet 506 to create a cylindrical shape for the inner balloon sheet 506. Likewise, the longitudinal edge 512 of the outer balloon sheet 502 will be the edge that seals the opposing longitudinal edge 512 of the outer balloon sheet to create a cylindrical shape for the outer balloon sheet 502. The outer balloon sheet 502 is slightly larger than the inner balloon sheet 506 so that the cylindrical shape of the outer sheet may fit on the outside of the cylindrical shape of the inner sheet. The sleeves 504 are outward facing on the outside of the outer balloon sheet's cylindrical form.

The inflation connection point 512 is where the balloon's inflation fluid enters and exists to inflate and deflate the balloon 118 respectively. The inflation connection point 512 connects to the inflation lumen 114 (FIG. 1). The inflation connection point 512 may be a hole or it may be an actual small valve connector to connect to the inflation lumen 114. In other embodiments, it may just be a marking on the inner balloon sheet to provide guidance to create a hole upon assembly and attachment of the balloon 118 to the catheter 106.

The sleeves 504 on the balloon 118 will create a channel to allow the suction line wrap 114 to remain securely attached to the balloon 118. Once the balloon 118 is inflated, the suction line wrap 114 fits securely in the helical groove 504 (FIG. 5) on the balloon 118. The suction line wrap 114 provides a slight protrusion over the balloon surface to provide a more secure and stable seal of the balloon and the trachael tube system 100 within the patient because the slight protrusion is that of the suction line wrap 114. The suction effect created by the suction line wrap 114 around the balloon 118 helps to securely seal the balloon with the tracheal walls The balloon 118 is shaped by fusing the two layers of the balloon sheets together where the outer balloon sheet 502 will have a sleeve 504 to allow the suction line 120 to lay within. One end of the balloon 118 is completely sealed to the catheter 106 proximal to suction line 120. The other distal end of the balloon will not be completely sealed to the catheter 106. Instead, the inner balloon layer 506 will be attached to the spine portion of the catheter 106 as displayed as the spinal sealant 402 (FIG. 4).

Figure 6A:
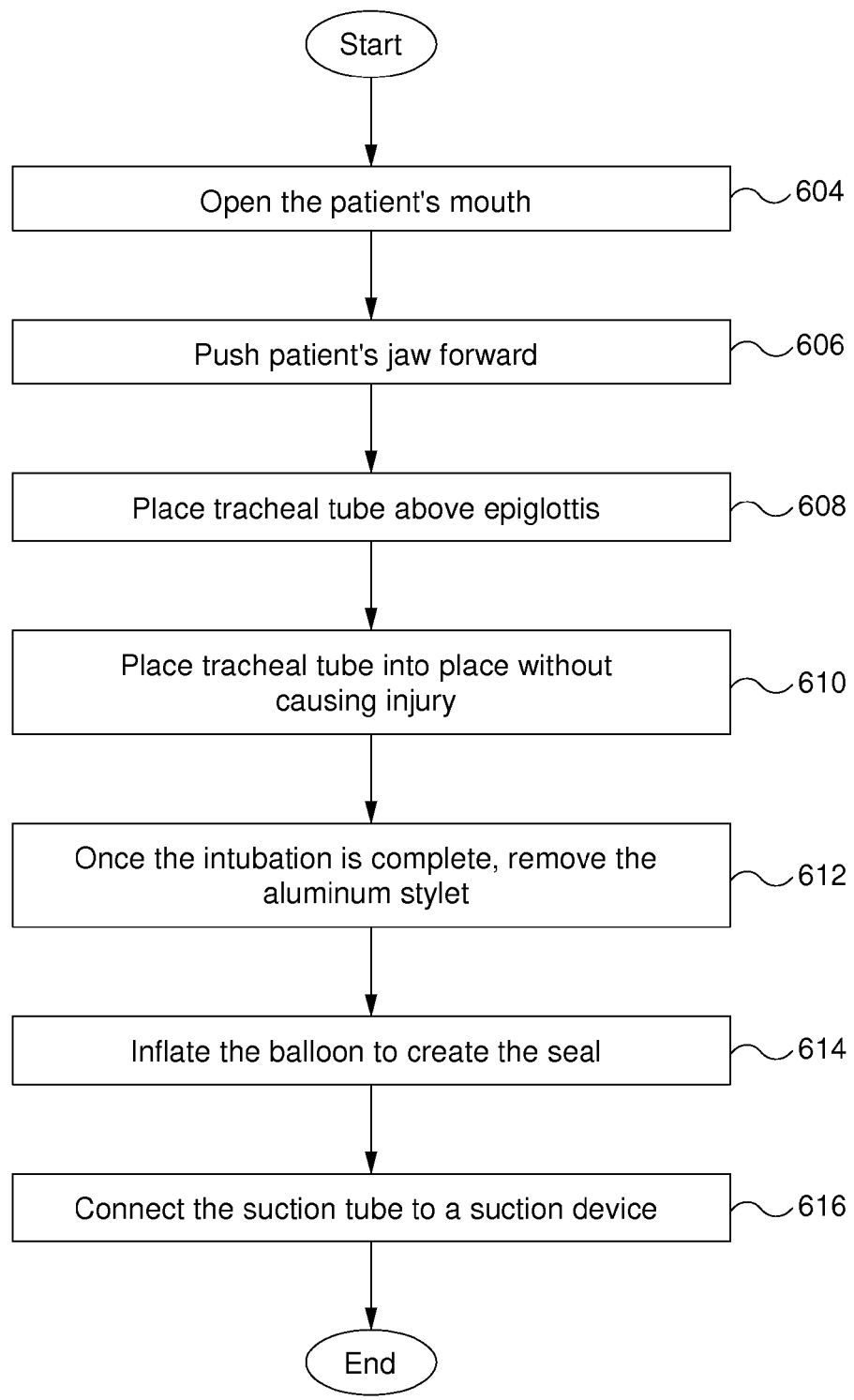
FIG. 6a shows a flowchart of an embodiment of a method for inserting the endotracheal tube.

FIG. 6a shows a flowchart of an embodiment of method 600a in which a caregiver is intubating a patient. In step 602, the caregiver determines that a patient needs an advance airway orally. In step 604, the caregiver opens the patient's mouth to begin the intubation process. In step 606, the caregiver pushes the patient's jaw forward to create an adequate opening to perform the intubation.

In step 608, the caregiver may use a laryngoscope as a guide to place the endotracheal tube above the epiglottis. The caregiver may also use a glidescope to assist with the intubation process. In some situations, where no guiding tools are available, the caregiver may intubate blindly if the situation requires immediate intubation. A laryngoscope is a medical device that is used to obtain a view of the vocal folds and the glottis. Laryngoscopy (larynx+scopy) may be performed to facilitate tracheal intubation. A glidescope is the first commercially available video laryngoscope. The glidescope incorporates a high resolution digital camera, connected by a video cable to a high resolution LCD monitor. It may be used for tracheal intubation to provide controlled mechanical ventilation. When using the laryngoscope or glidescope to facilitate intubation, the caregiver should exercise special care to identify the vocal chords in order to properly intubate the tracheal tube to prevent contact between the balloon 118 and the vocal chords. If the caregiver does not properly intubate the tracheal tube below the vocal chord and if upon inflation of the balloon 118 the cuff expands onto the vocal chord, it may damage the patient's vocal chord. Extra care must be exercised to ensure the intubation is performed correctly and the vocal chords are clear of contact by the balloon once the balloon 118 is inflated. An aluminum stylet may be used to provide the flexible endotracheal tube with some support and stiffness to assist with the intubation process.

In step 610, the caregiver places the tracheal tube into place properly without causing injury. Injuries may include breaking teeth or damaging vocal chords. In step 612, once the intubation is complete, the caregiver removes the aluminum stylet from the tracheal tube.

In step 614, the caregiver inflates the balloon with air by attaching a syringe or any other fluid providing device that may be required to inflate the balloon. In some embodiments, air may be the fluid of choice. In other embodiments, a liquid based fluid may be used. When the balloon is inflated, the coiled suction line 120 form fits into the sleeves on the outside of the balloon.

In step 615, the caregiver deploys the suction line 120 and the balloon is inflated to the tracheal border.

In step 616, the caregiver connects the suction tube 108e to a suction device 108a to provide a constant stream of suction to the region bordered by the cuff and trachea above the balloon 118. The suction device may have a suction power adjustable knob to set a desired suction. By connecting the suction tube 108e to the suction device 108a, the removal of secretion build up located above the balloon 118 and between the tracheal walls and the balloon may continue indefinitely without the need for a caregiver to constantly monitor the patient for secretion build up.

In step 617, the suction line 120 creates a seal between the balloon 118 and the trachea.

In an embodiment, each of the steps of method 600a is a distinct step. In another embodiment, although depicted as distinct steps in FIG. 6a, steps 604-617 may not be distinct steps. In other embodiments, method 600a may not have all of the above steps and/or may have other steps in addition to or instead of those listed above. The steps of method 600a may be performed in another order. Subsets of the steps listed above as part of method 600a may be used to form their own method.

Figure 6B:
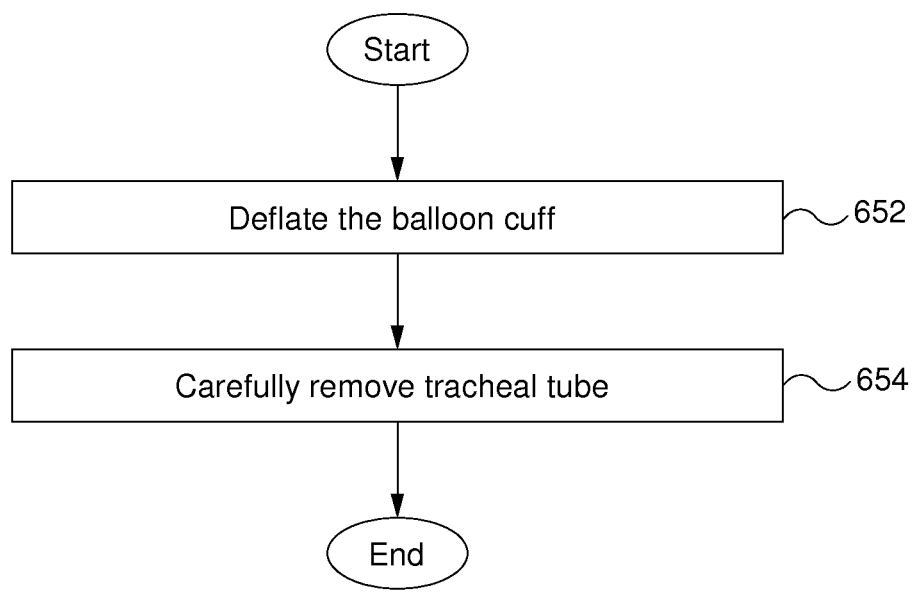
FIG. 6b shows a flowchart of an embodiment of a method for removing the endotracheal tube.

FIG. 6b shows a flowchart of an embodiment of method 600b in which a caregiver is removing an endotracheal tube. In step 652, the caregiver deflates the balloon 118 by pressing the pilot balloon 110b. In step 654, the caregiver carefully removes the endotracheal tube from the patient orally.

In an embodiment, each of the steps of method 600b is a distinct step. In another embodiment, although depicted as distinct steps in FIG. 6b, step 652-654 may not be distinct steps. In other embodiments, method 600b may not have all of the above steps and/or may have other steps in addition to or instead of those listed above. The steps of method 600b may be performed in another order. Subsets of the steps listed above as part of method 600b may be used to form their own method.

Figure 7A:
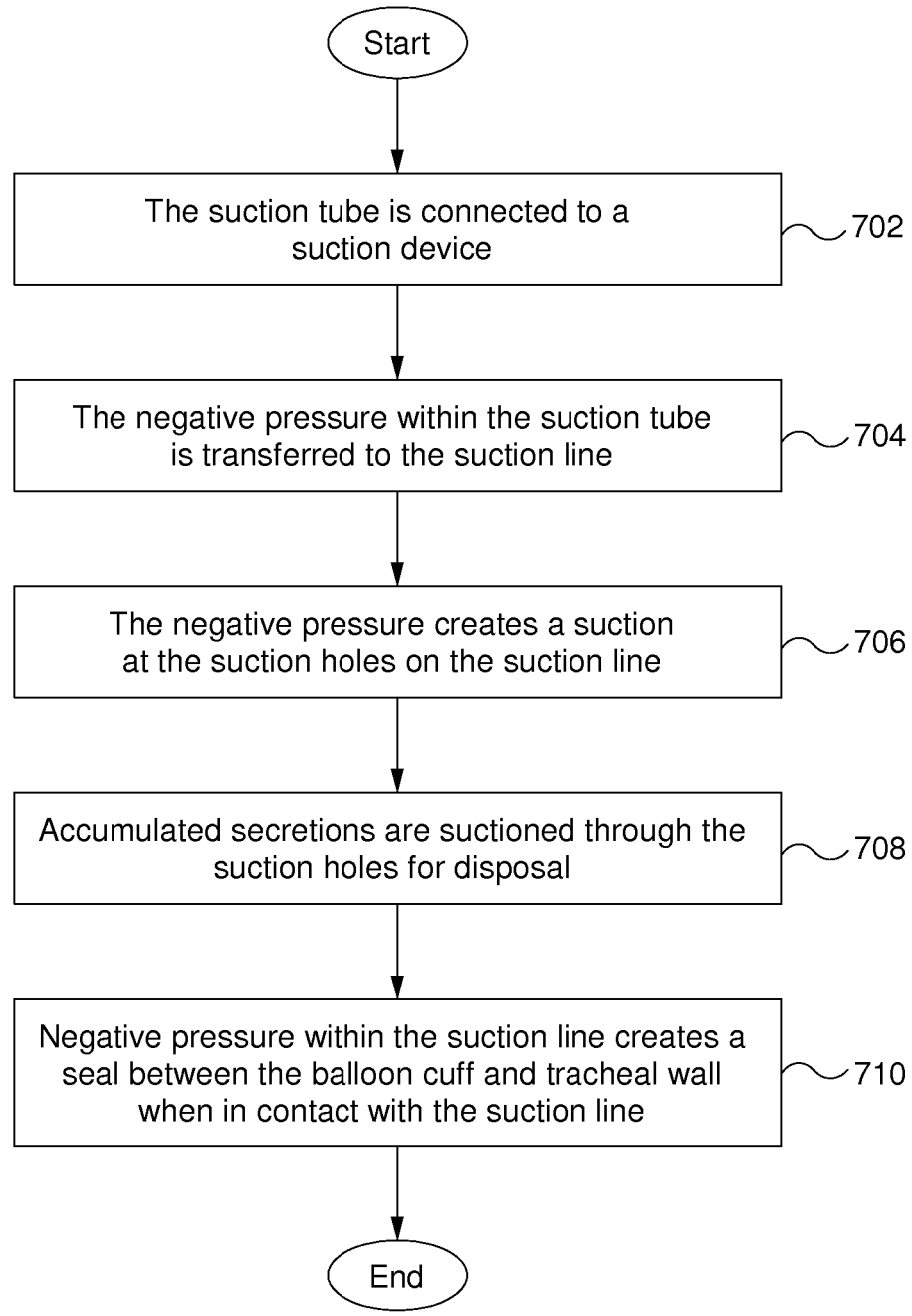
FIG. 7a shows a flowchart of an embodiment of a method for suctioning secretion from the border of the cuff and trachea region.

FIG. 7a shows a flowchart of an embodiment of method 700a in which a suctioning device is suctioning secretion from the region bordered by the cuff and trachea. In step 702, the suction tube 108e is connected to a suction device 108a. In step 704, the negative pressure within the suction tube 108e is transferred through the suction tube lumen 112 to the suction line 120. In step 706, the negative pressure creates a negative pressure/suction at the suction holes throughout the suction line 120. In step 708, the accumulated secretions are suctioned through the suction holes for disposal. In step 710, the negative pressure within the suction line creates a seal between the balloon 118 and the patient's tracheal wall. The secretions may be collected for samples for culture for diagnosing and monitoring.

In an embodiment, each of the steps of method 700a is a distinct step. In another embodiment, although depicted as distinct steps in FIG. 7a, step 702-710 may not be distinct steps. In other embodiments, method 700a may not have all of the above steps and/or may have other steps in addition to or instead of those listed above. The steps of method 700a may be performed in another order. Subsets of the steps listed above as part of method 700a may be used to form their own method.

Figure 7B:
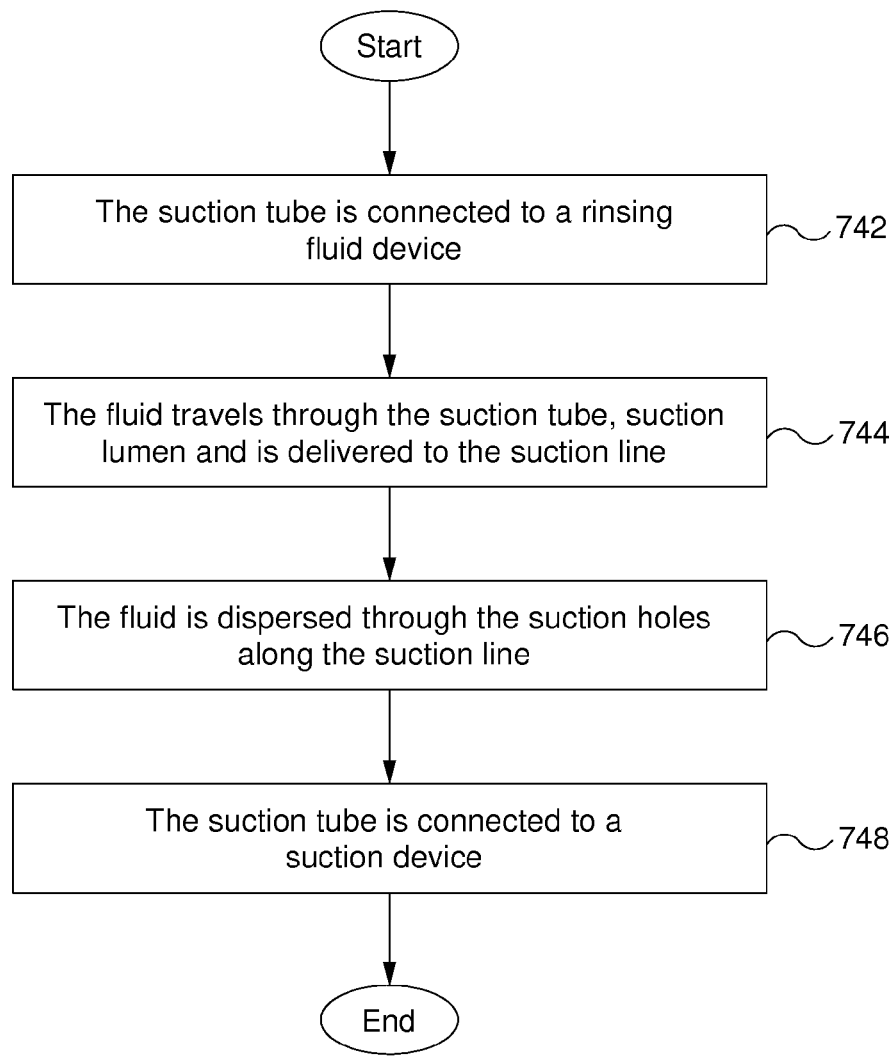
FIG. 7b shows a flowchart of an embodiment of a method for rinsing fluid dispensing device is applying a rinsing fluid.

FIG. 7b shows a flowchart of an embodiment of method 700b in which a rinsing fluid dispensing device is applying a rinsing fluid. In step 742, the suction tube 108e is connected to a rinsing fluid device 108c. In step 744, the rinsing fluid travels through the suction tube 108e, the suction tube lumen 112, and the suction line 120. In step 746, the rinsing fluid is dispersed through the suction holes on the suction line 120. The rinsing fluid is allowed to momentarily interact with the mucous and area bordered by the cuff and trachea. Depending on the rinsing fluid used, the mucous may be loosened to allow it to be easily extracted. In step 748, the suction tube 108e is reconnected to a suction device 108a to remove the rinsing fluid and any other secretion that may have collected during the rinsing fluid administering process.

In an embodiment, each of the steps of method 700b is a distinct step. In another embodiment, although depicted as distinct steps in FIG. 7b, step 742-748 may not be distinct steps. In other embodiments, method 700b may not have all of the above steps and/or may have other steps in addition to or instead of those listed above. The steps of method 700b may be performed in another order. Subsets of the steps listed above as part of method 700b may be used to form their own method.

Figure 7C:
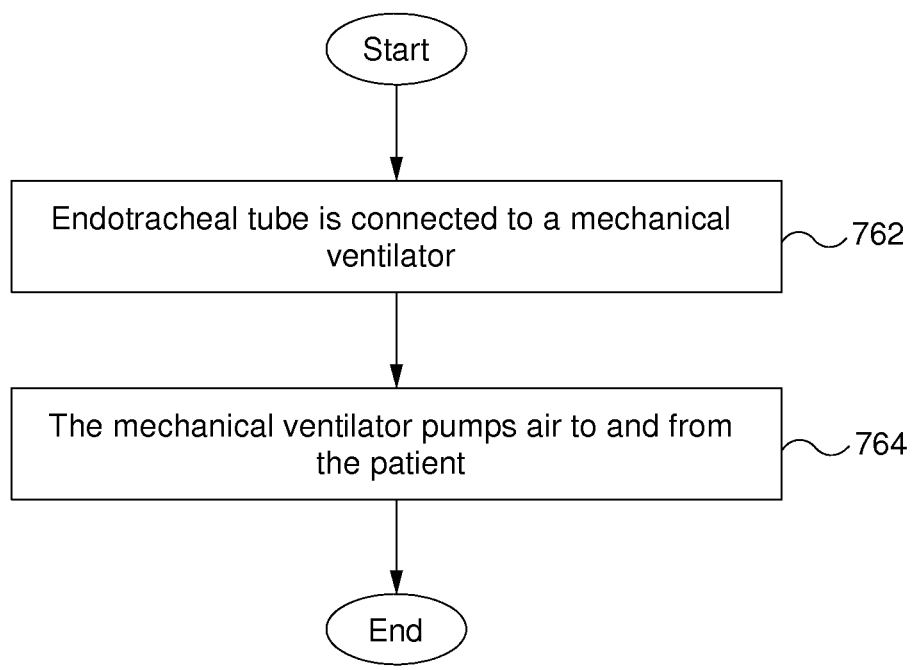
FIG. 7c shows a flowchart of an embodiment of a method for artificially ventilating a patient.

FIG. 7c shows a flowchart of an embodiment of method 700c in which a mechanical ventilator is artificially ventiliating a patient. In step 762, a tracheal tube system 100 is connected to a mechanical ventilator via connector 102. In step 764, the mechanical ventilator pumps air to and from the patient's lung(s) by way of a primary channel 107, the enlarged opening 124, and the open distal end 122. The velocity of oxygen and air flowing into the patient's lungs is reduced as a result of the enlarged opening 124 and the enlarged air passage way 126.

In an embodiment, each of the steps of method 700c is a distinct step. In another embodiment, although depicted as distinct steps in FIG. 7c, step 762-764 may not be distinct steps. In other embodiments, method 700c may not have all of the above steps and/or may have other steps in addition to or instead of those listed above. The steps of method 700c may be performed in another order. Subsets of the steps listed above as part of method 700c may be used to form their own method.

Figure 8:
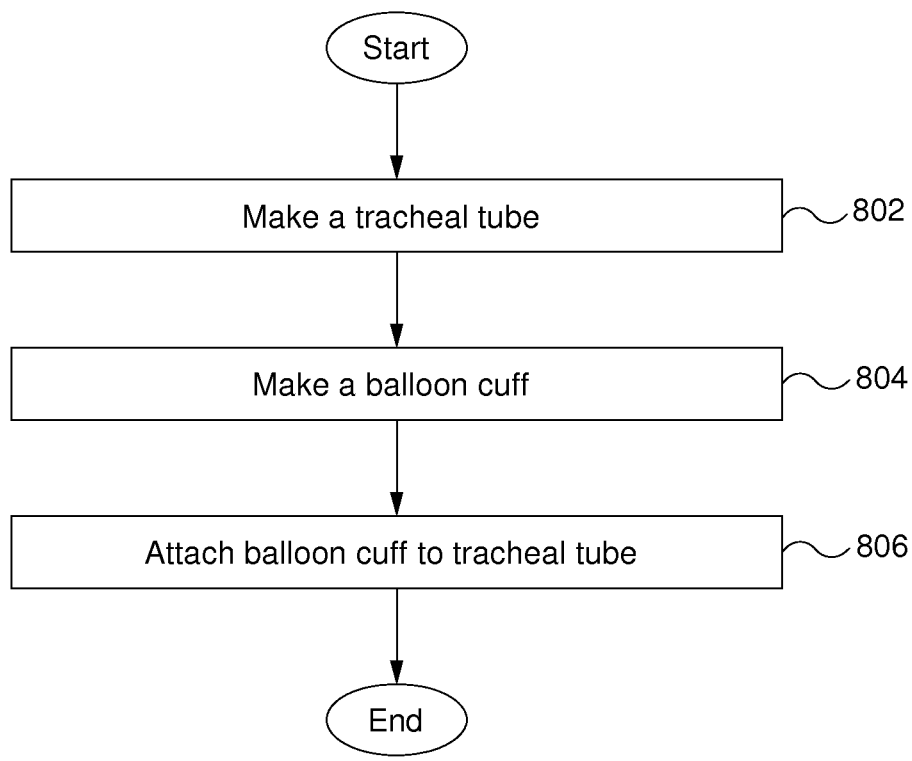
FIG. 8 shows a flowchart of an embodiment of a method manufacturing a tracheal tube.

FIG. 8 shows a flowchart of an embodiment of method 800 in which a tracheal tube of system 100 is manufactured. In step 802, a tracheal tube is made. In step 804, a balloon 118 is made, which involves the step of making the balloon 118. In step 806, the balloon 118 is attached to the tracheal tube from step 802. In other embodiments of method 800, step 804 may be performed before step 802. However, step 806 requires that step 802 and step 804 are performed in order to attach the tracheal tube and the balloon 118.

In an embodiment, each of the steps of method 800 is a distinct step. In another embodiment, although depicted as distinct steps in FIG. 8, step 802-806 may not be distinct steps. In other embodiments, method 800 may not have all of the above steps and/or may have other steps in addition to or instead of those listed above. The steps of method 800 may be performed in another order. Subsets of the steps listed above as part of method 800 may be used to form their own method.

Figure 9:
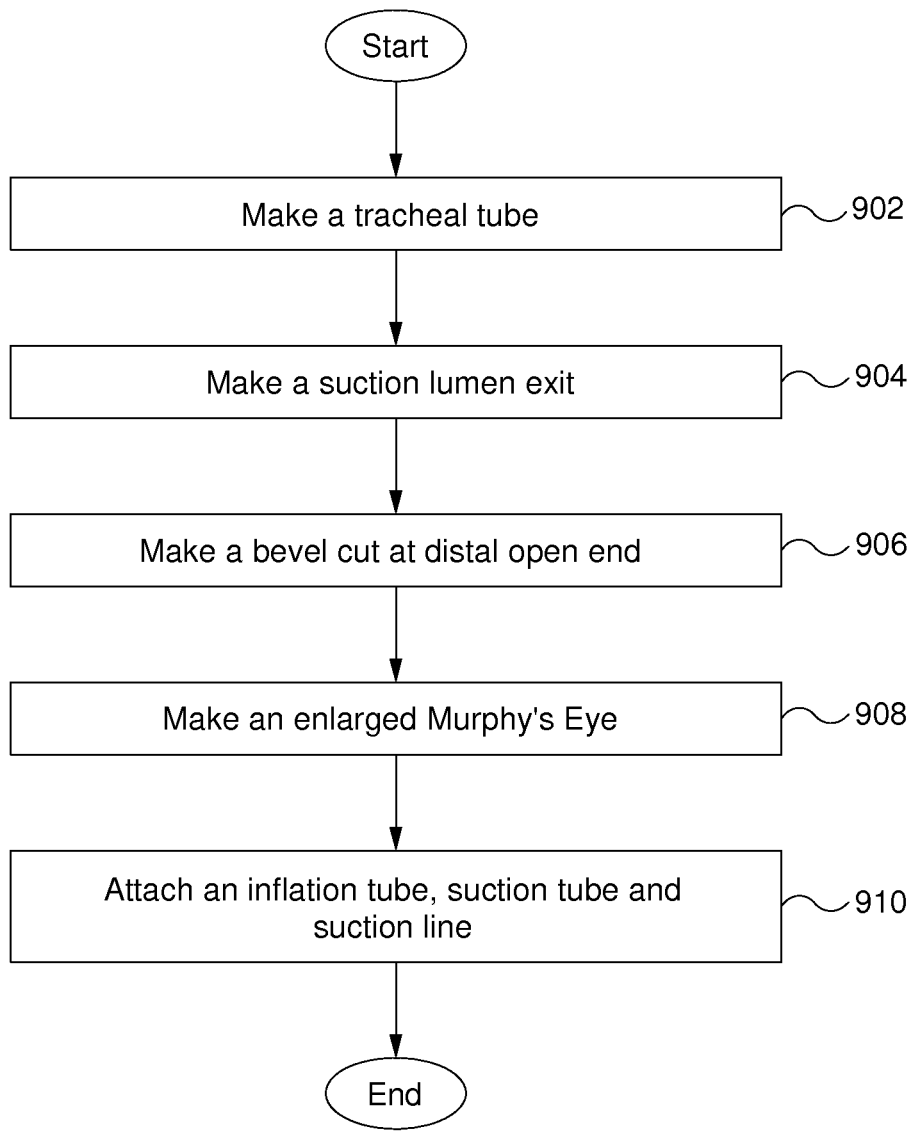
FIG. 9 shows a flowchart of an embodiment of a method for manufacturing a tracheal tube.

FIG. 9 shows a flowchart of an embodiment of a method for implementing step 802 in which a tracheal tube system 100 is manufactured. In step 902, a tracheal tube is made, which may include making a catheter 106 from a plastic (polyvinyl chloride, PVC) material with 3 lumen comprising a suction lumen 108e, an inflation lumen 110a and a primary channel 107. In other embodiments, other types of material may be used to make the catheter 106 such as wire-reinforced silicone, silicone rubber, latex rubber, or stainless steel. The length, diameter, and thickness of the catheter 106 may vary depending on the size of the catheter being created for the various ages, genders and sizes of a targeted user base. The suction lumen 108e and inflation lumen 110a are built into the wall of the catheter 106. In other embodiments, the suction lumen 108e and inflation lumen 110a may be tubes attached on the outer surfaces of catheter 106.

In step 904, make a suction lumen exit 116. The suction lumen exit 116 is an exit hole at the distal end of the suction lumen 108e proximal to the balloon 118. The suction lumen exit 116 may be located slightly above the point where the balloon 118 will be attached to the catheter 106.

In step 906, a bevel cut is made at open distal end 122. The bevel shape of the catheter 106 helps with the intubation process of the tracheal tube.

In step 908, an enlarged opening 124 is made. Step 908 involves cutting an elongated oval shaped opening proximal to the open distal end 122 on the top side of the catheter 106. The length of the enlarged opening 124 is extended along the length of the catheter 106 starting proximal to the open distal end 122 and extending proximal to the suction lumen exit hole 116.

In step 910, an inflation tube 110a, suction tube 108e, and suction line 120 is attached to the catheter 106. An inflation tube 110a is attached to the inflation lumen 114 on one end and to a pilot balloon 110b on the opposite end. In another embodiment, inflation tube 110a may be an extension of inflation lumen 114 and a part of step 902. In other embodiments, pilot balloon 110b may be attached to the inflation tube prior to intubation.

A suction tube 108e is attached to the suction tube lumen 112. In another embodiment, suction tube 108e may be an extension of suction tube lumen 112 and a part of step 902.

A suction line 120 is attached to the suction lumen exit 116. The suction line 118 may be similar to the suction tube 108e in material, shape, and diameter. However, the suction line 120 contains many small holes distributed throughout the suction line 120 in order to provide fluid transmission in and out of the suction line 120. In another embodiment, the suction line 120 may be an extension of the suction lumen 112 and a part of the suction lumen exit 116.

In step 912, a preformed balloon cuff is attached to the balloon 118.

In an embodiment, each of the steps of method 802 is a distinct step. In another embodiment, although depicted as distinct steps in FIG. 9, step 902-912 may not be distinct steps. In other embodiments, method 802 may not have all of the above steps and/or may have other steps in addition to or instead of those listed above. The steps of method 802 may be performed in another order. Subsets of the steps listed above as part of method 802 may be used to form their own method.

Figure 10:
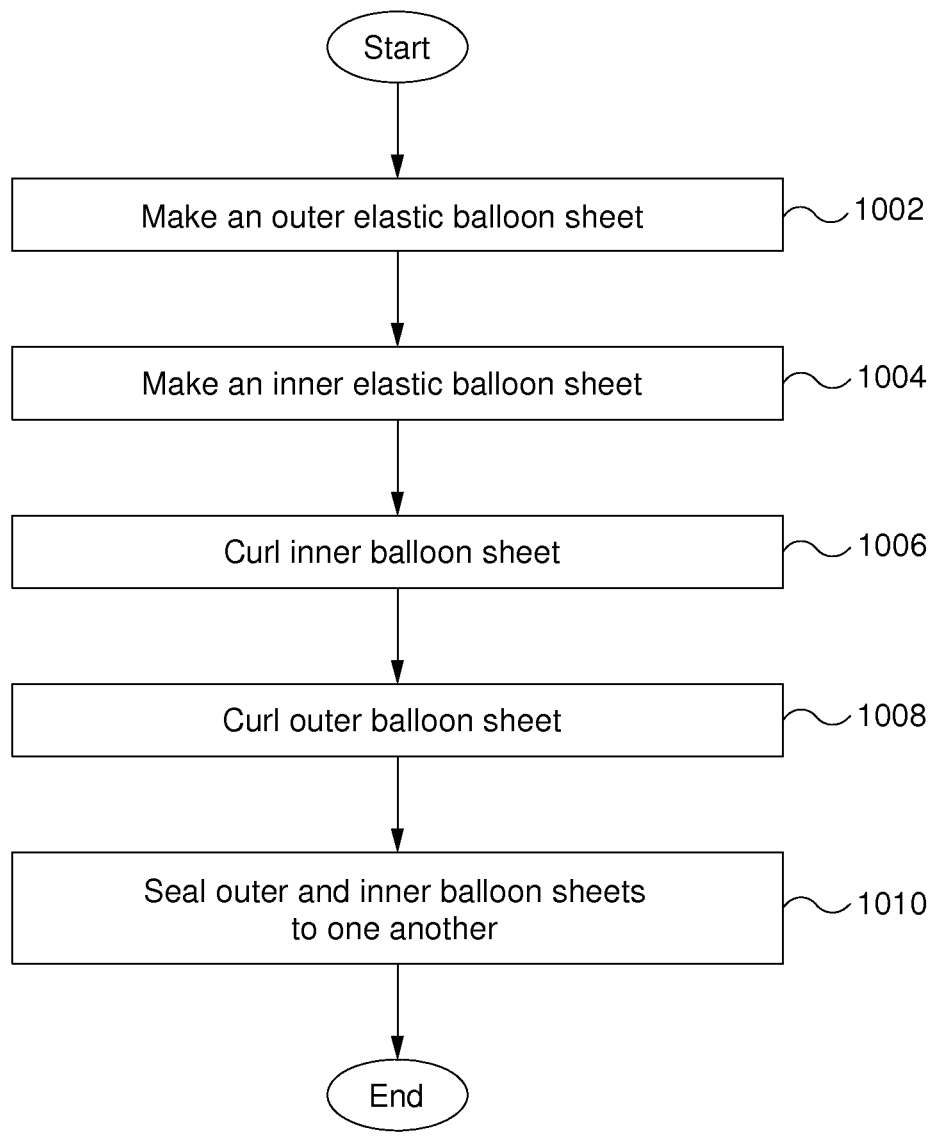
FIG. 10 shows a flowchart of an embodiment of a method for creating a balloon.

FIG. 10 shows a flowchart of an embodiment of a method of implementing step 804 in which a balloon is manufactured. In step 1002, an outer balloon sheet 502 is made using a flexible rubber based thin sheet that is generally used in balloon manufacturing for endotracheal tubes. The outer balloon sheet 502 comprises a plurality of sleeves 504 arranged diagonally across the sheet to serve as channels for the suction line 120 to fit into when the balloon 118 is inflated. The diagonally aligned sleeves on the outer balloon sheet 502, when curled lengthwise and attached, creates a helical groove for the suction line 120. The shape of the outer sheet is displayed in FIG. 5.

In step 1004, an inner balloon sheet 506 is made using a similar material as the material used in step 1002 when making the outer balloon sheet 502. The inner balloon sheet 506 is the same shape as the outer balloon sheet 502. The inner balloon 506 does not contain sleeves arranged diagonally across the sheet.

In step 1006, the inner balloon sheet 506 is curled into a cylindrical shape and sealed along the longitudinal edge 512. In step 1008, the outer balloon sheet 502 is curled into a cylindrical shape and sealed along its longitudinal edge 512.

In step 1010, the outer balloon sheet 502 and inner balloon sheet 506 are sealed to one another along the distal edge 510 and the balloon connection point 508. The outer balloon sheet 502 is on the outside of the connection with the sleeves 504 facing outwards. The balloon connection point 508 is sealed completely to ensure there will be no spaces for air to inflate in connection point 508 area of the balloon assembly.

In an embodiment, each of the steps of method 804 is a distinct step. In another embodiment, although depicted as distinct steps in FIG. 10, step 1002-1010 may not be distinct steps. In other embodiments, method 804 may not have all of the above steps and/or may have other steps in addition to or instead of those listed above. The steps of method 804 may be performed in another order. Subsets of the steps listed above as part of method 804 may be used to form their own method.

Figure 11:
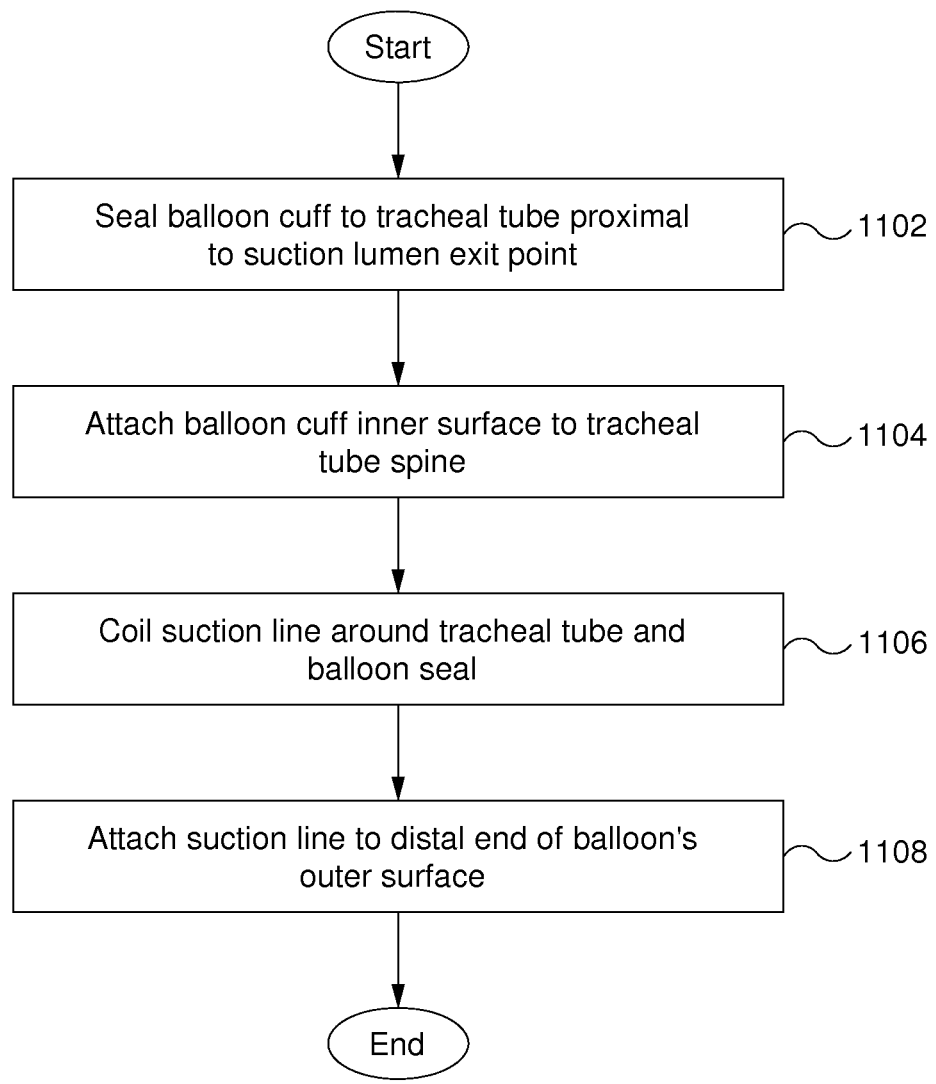
FIG. 11 shows a flowchart of an embodiment of a method for attaching a balloon to the endotracheal tube.

FIG. 11 shows a flowchart of an embodiment of a method for implementing step 806 in which a balloon is attached to a tracheal tube. The attachment of the balloon 118 assembled from step 804 and tracheal tube assembled from step 802. In step 1102, the the balloon 118 is attached to the tracheal tube assembled from step 802 by inserting the distal end 122 through the balloon 118 from the connection point 508 towards the distal edge 510. The connection point 508 is sealed completely around the catheter 106 proximal to the suction lumen exit 116 without coming into contact with the suction lumen exit 116.

In step 1104, the inner surface of the balloon 118 is sealed to the spinal length of the catheter 106 along the spinal seal 402. The spinal seal 402 does not contact or obstruct the enlarged opening 124. The inflation lumen 114 is connected to the balloon 118 at the inflation connection point 512. In step 1106, the suction line 120 is coiled around the catheter 106 from the suction lumen exit 116 towards the distal end 122. The suction line 120 is further coiled around the deflated balloon 118 guided by the helical groove created by the sleeves 504.

In step 1108, the suction line 120 is attached to the outer surface of the distal end of balloon 118. The attached point may be proximal along the distal edge 510 of the balloon, without actually coming into contact with the sealed distal edge 510.

In an embodiment, each of the steps of method 806 is a distinct step. In another embodiment, although depicted as distinct steps in FIG. 11, step 1102-1108 may not be distinct steps. In other embodiments, method 806 may not have all of the above steps and/or may have other steps in addition to or instead of those listed above. The steps of method 806 may be performed in another order. Subsets of the steps listed above as part of method 806 may be used to form their own method.

ALTERNATIVES AND EXTENSIONS

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A tracheal tube system comprising:
   a first tube that is flexible and hollow allowing air to pass through, the first tube having a first end and a second end;
   a balloon attached to the first tube, the balloon being positioned between the first and second ends of the tube and having a shape and size such that when inflated, the balloon forms a second tube surrounding the first tube; and
   a third tube having a multiplicity of holes and being configured to be coupled to a suction device, the third tube being coincident with a portion of an outer wall of the balloon and being oriented in a direction substantially perpendicular to the first tube.

2. The tracheal tube system of claim 1, wherein the first tube has a length, the balloon being attached along a line on an outer wall of the first tube and an inner layer of the balloon, the line extending along the length of the first tube.

3. The tracheal tube system of claim 1, wherein the balloon is coupled to an inflation tube at an orifice opening into the balloon and air pumped into the inflation tube enters the orifice opening between an inner wall of the balloon and the outer wall of the balloon to inflate the balloon.

4. The tracheal tube system of claim 1, wherein the tracheal tube system is inserted into a trachea of a patient and negative pressure in the third tube creates suction pulling at least one of the third tube and the balloon toward an interior wall of the trachea.

5. The tracheal tube system of claim 4, the outer wall of the balloon being shaped to have a channel when inflated, the channel being shaped and positioned so as to accommodate placement of the third tube therein.

6. The tracheal tube system of claim 4, wherein the first tube has a lumen and the third tube is coupled to the lumen so that negative pressure in the lumen causes negative pressure in the third tube, thereby creating the suction.

7. The tracheal tube system of claim 6, wherein the lumen has a first opening attached to the third tube and a second opening attached to a fourth tube.

8. The tracheal tube system of claim 7, wherein the balloon is coupled to an inflation tube at an orifice opening into the balloon so that air pumped into the inflation tube enters the orifice opening and accumulates in the balloon so as to inflate the balloon.

9. The tracheal tube system of claim 8, wherein the first tube has a second lumen and a first end of the second lumen is coupled to an inflation tube and the balloon is coupled to the second end of the second lumen.

10. A tracheal tube system comprising:
    a first tube that is flexible and hollow;
    the first tube having a first end that is open and a second end that is open, therein allowing air to flow into the first end, through the tube, and out the second end;
    a balloon attached to the first tube between the first end of the first tube and the second end of the first tube and surrounding a portion of the first tube, the balloon forming a second flexible tube surrounding the portion of the first tube when inflated; and
    a third tube having a multiplicity of holes along sidewalls of the third tube, the third tube being coincident with an indentation located on a portion of an outer wall of the balloon.

* * * * *